(12) United States Patent
Sullivan et al.

(10) Patent No.: US 9,328,246 B2
(45) Date of Patent: *May 3, 2016

(54) NONPOLYMERIC ANTIREFLECTION COMPOSITIONS CONTAINING ADAMANTYL GROUPS

(71) Applicant: Brewer Science Inc., Rolla, MO (US)

(72) Inventors: Daniel M. Sullivan, Rolla, MO (US); Charlyn Stroud, St. James, MO (US); Jinhua Dai, Rolla, MO (US)

(73) Assignee: Brewer Science Inc., Rolla, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/743,965

(22) Filed: Jan. 17, 2013

(65) Prior Publication Data

US 2013/0186851 A1 Jul. 25, 2013

Related U.S. Application Data

(60) Provisional application No. 61/588,268, filed on Jan. 19, 2012.

(51) Int. Cl.
| | | |
|---|---|---|
| *G03F 7/11* | (2006.01) | |
| *G03F 7/40* | (2006.01) | |
| *C09D 5/00* | (2006.01) | |

(Continued)

(52) U.S. Cl.
CPC .............. *C09D 5/006* (2013.01); *C07C 69/76* (2013.01); *C07C 69/94* (2013.01); *C07D 303/23* (2013.01); *G03F 7/091* (2013.01); *G03F 7/094* (2013.01); *G03F 7/30* (2013.01); *G03F 7/40* (2013.01); *C07C 2103/24* (2013.01); *C07C 2103/74* (2013.01); *H01L 21/0276* (2013.01); *Y10T 428/265* (2015.01); *Y10T 428/31511* (2015.04); *Y10T 428/31525* (2015.04); *Y10T 428/31529* (2015.04)

(58) Field of Classification Search
None
See application file for complete search history.

(56) References Cited

U.S. PATENT DOCUMENTS 5,858,618 A * 1/1999 Tzou .......................... 430/285.1
7,790,917 B2    9/2010 Okada et al.
(Continued)

FOREIGN PATENT DOCUMENTS

CN      102311346 A  *  1/2012
JP      2005126685      5/2005
(Continued)

OTHER PUBLICATIONS

Abstract and structures of CN 102311346a published Jan. 11, 2012, the abstract being DERWENT-ACC-No. 2012=B49618 and 6 pages . . . .*

(Continued)

*Primary Examiner* — Cynthia Hamilton
(74) *Attorney, Agent, or Firm* — Hovey Williams LLP

(57) ABSTRACT

Nonpolymeric compounds, compositions, and methods for forming microelectronic structures, and the structures formed therefrom are provided. The nonpolymeric compounds are ring-opened, epoxide-adamantane derivatives that comprise at least two epoxy moieties and at least one adamantyl group, along with at least one chemical modification group, such as a chromophore, bonded to a respective epoxy moiety. Antireflective and/or planarization compositions can be formed using these compounds and used in lithographic processes, including fabrication of microelectronic structures.

18 Claims, 3 Drawing Sheets

(51) Int. Cl.
G03F 7/30 (2006.01)
G03F 7/09 (2006.01)
C07D 303/23 (2006.01)
C07C 69/76 (2006.01)
C07C 69/94 (2006.01)
H01L 21/027 (2006.01)

(56) References Cited

U.S. PATENT DOCUMENTS

| | | | |
|---|---|---|---|
| 8,017,800 | B2 | 9/2011 | Okada et al. |
| 2005/0181299 | A1 | 8/2005 | Trefonas, III et al. |
| 2005/0277058 | A1 | 12/2005 | Iwabuchi et al. |
| 2009/0062481 | A1* | 3/2009 | Ito et al. .................. 525/418 |
| 2009/0099330 | A1* | 4/2009 | Okada et al. ................ 528/98 |
| 2009/0297784 | A1 | 12/2009 | Xu et al. |
| 2010/0056663 | A1 | 3/2010 | Ito et al. |
| 2010/0213580 | A1 | 8/2010 | Meador et al. |
| 2013/0280656 | A1* | 10/2013 | Lowes et al. .............. 430/280.1 |

FOREIGN PATENT DOCUMENTS

| | | | | |
|---|---|---|---|---|
| JP | 2009020501 | A | * | 1/2009 |
| JP | 2009093162 | A | * | 4/2009 |
| JP | 2010-186174 | A | * | 8/2010 |
| JP | 2010-224158 | A | * | 10/2010 |
| JP | 2010-230773 | A | * | 10/2010 |
| JP | 2010-250180 | A | * | 11/2010 |

OTHER PUBLICATIONS

English translation of JP 2010-230773, A (2010) from machine translation from AIPN Japan Patent Office National center for Industrial Property Information and Training, generated Aug. 15, 2013, 24 pages.*

English translation of JP,2010-224158, A (2010) from machine translation from AIPN Japan Patent Office National Center for Industrial Property Information and Training, generated Oct. 27, 2013, 23 pages.*

English translation of JP,2010-186174, A (2010) from machine translation from AIPN Japan Patent Office National Center for Industrial Property Information and Training, generated Oct. 27, 2013, 45 pages and 14 pages.*

English translation of JP,2010-250180 , A (2010) from machine translation from AIPN Japan Patent Office National Center for Industrial Property Information and Training, generated Oct. 27, 2013, 22 pages.*

English translation of JP, 2009-093162 , A (2009) from machine translation from AIPN Japan Patent Office National Center for Industrial Property Information and Training, generated Mar. 6, 2014, 29 pages.*

English translation of JP 2009-020501, A (2009) from machine translation from AIPN Japan Patent Office National Center for Industrial Property Information and Training, generated Sep. 18, 2014, 66 pages (42 of 42 and 24 of 24).*

Meador et al., "Improving the performance of light-sensitive developer-soluble anti-reflective coatings by using adamantyl terpolymers," Proc. SPIR, 2009, 727312-1-727312-9, 7273.

International Search Report and Written Opinion dated Apr. 30, 2013 in Application No. PCT/US2013/021932 filed Jan. 17, 2013.

Machine Translation of JP2005126685, 22 pages.

* cited by examiner

NONPOLYMERIC ANTIREFLECTION COMPOSITIONS CONTAINING ADAMANTYL GROUPS

CROSS-REFERENCE TO RELATED APPLICATIONS

The present application claims the priority benefit of U.S. Provisional Patent Application Ser. No. 61/588,268, filed Jan. 19, 2012, entitled NONPOLYMERIC ANTIREFLECTION COMPOSITIONS CONTAINING ADAMANTYL GROUPS, incorporated by reference in its entirety herein.

BACKGROUND

1. Field of the Invention

The present invention relates to compositions comprising nonpolymeric adamantyl compounds useful as anti-reflective coatings and/or planarization layers in lithography processes, including microelectronics fabrication processes.

2. Description of Related Art

Integrated circuit manufacturers are consistently seeking to maximize wafer sizes and minimize device feature dimensions in order to improve yield, reduce unit cost, and increase on-chip computing power. Improvements in lithography techniques and smaller-wavelength photolithography radiation sources now allow features close to 20 nm to be created. Reducing and/or optimizing the substrate reflectivity during photoresist exposure is critical for maintaining dimension control of such small features. Therefore, light absorbing organic polymers known as antireflective coatings are applied beneath photoresist layers in order to reduce the reflectivity normally encountered from the semiconductor substrates during the photoresist exposure.

Prior art anti-reflective coating layers contain a polymeric resin with a light-absorbing chromophore either attached to, or blended with, the resin. Although high optical densities enable these polymers to provide effective reflectivity control, they also have numerous drawbacks. For example, these polymers have high molecular weights that cause problems during polymer blending. More particularly, the use of these polymers inhibits customization of the antireflective coating to the photoresist being employed in the particular photolithographic process. Customization is extremely important because it allows for straighter profiles and better adhesion of the photoresist to the anti-reflective coating, thus resulting in better performance. Lower molecular weight components also allow better flow properties, which increase the material's ability to fill topography on the device surface and create a more planar surface for the photoresist application. Thus, there remains a need in the art for improved anti-reflective or planarization coating compositions.

SUMMARY

The present disclosure is broadly concerned with compounds, compositions, and methods for forming microelectronic structures, and the structures formed therefrom. In one or more embodiments, the methods comprise providing a microelectronic substrate having a surface; optionally forming one or more intermediate underlayers on the substrate surface; and forming an anti-reflective or planarization layer adjacent the intermediate layers, if present, or adjacent the substrate surface if no intermediate layers are present. The anti-reflective or planarization layer is formed from a composition comprising a nonpolymeric compound dispersed or dissolved in a solvent system. The nonpolymeric compound comprises at least two epoxy moieties and at least one adamantyl group.

Anti-reflective or planarization compositions useful in forming microelectronic structures are also disclosed herein. The compositions comprise a nonpolymeric compound dispersed or dissolved in a solvent system. The nonpolymeric compound comprises at least two epoxy moieties and at least one adamantyl group, wherein at least one of the epoxy moieties comprises a chemical modification group.

Microelectronic structures are also described herein. In one or more embodiments, the microelectronic structures comprise a microelectronic substrate having a surface; optionally, one or more intermediate underlayers on the substrate surface; and an anti-reflective or planarization layer adjacent the intermediate underlayers, if present, or adjacent the substrate surface if no intermediate underlayers are present. The anti-reflective or planarization layer is formed from a composition comprising a nonpolymeric compound dispersed or dissolved in a solvent system. The nonpolymeric compound comprising at least two epoxy moieties and at least one adamantyl group.

A nonpolymeric compound comprising a core component, with at least two epoxy moieties and at least one adamantyl group respectively bonded to the core component is also disclosed herein. In one or more embodiments, at least one of the epoxy moieties of the formula:

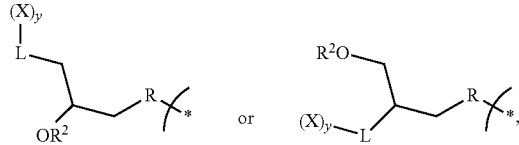

wherein * is the attachment point to the compound, each y is 1-2, each X is a chemical modification group, each L is individually an amino, ether, thio (thioether), hydrazine, sulfinate, sulfonate, sulfonamide, ester, carbonate, carbamate, amide, or urea linkage, each R is individually —O— or —CH$_2$—, and each R$^2$ is individually an —H, alkyl, sulfonate, ester, carbonate, carbamate, or functionalized derivative thereof.

DETAILED DESCRIPTION OF THE PREFERRED EMBODIMENTS

Figure 1:
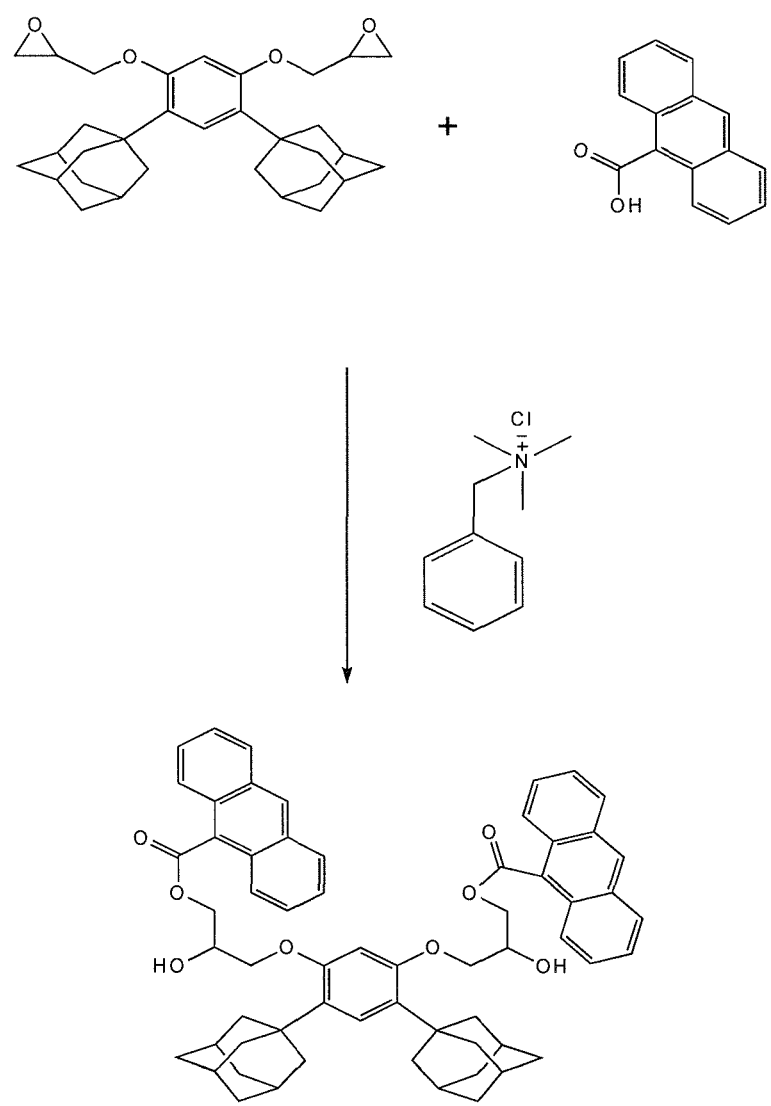
FIG. 1 is a reaction scheme for formation of a nonpolymeric compound according to an embodiment of the invention by reacting 9-anthracenecarboxylic acid with 1,3-bis(1-adamantyl)-4,6-bis(glycidyloxy)benzene.

The present disclosure is concerned with compositions useful as anti-reflective coatings and/or planarization (aka gap-fill) layers, where the compositions comprise large, nonpolymeric molecules with high carbon content and methods of using the same. The invention overcomes problems encountered in the prior art by providing compositions comprising low molecular weight, customizable components with high etch resistance. The inventive compositions comprise (consist essentially, or even consist of) a nonpolymeric compound dissolved or dispersed in a solvent system. The term "nonpolymeric" is used to signify that the compounds do not have a polymer (or oligomer) backbone comprised of repeating units typically created through polymerization, and thereby distinguish the present compounds from oligomers and/or polymers. The term is more specifically defined herein as referring to molecular compounds having a weight average molecular weight of less than about 3,000 Daltons or compounds having less than about 10 monomeric repeat units. In other words, it will be appreciated that some nonpolymeric compounds or molecules may have large molecular weights above 3,000 Daltons, but are nonetheless nonpolymeric as having less than about 10 monomeric repeat units. The term "polymeric" is used synonymously herein with "oligomeric" and is defined as referring to compounds having a backbone with more than 10 monomeric repeat units. In one or more embodiments, nonpolymeric compounds according to the invention have no repeat units and/or no polymeric (oligomeric) backbone.

The nonpolymeric compounds each comprise at least two epoxy moieties and at least one adamantyl group. The term "epoxy moiety" is used herein to refer to both closed epoxide rings as well as ring-opened (reacted) epoxy groups. The term "adamantyl groups" refers to substituted or unsubstituted adamantane functional groups that can be pendant from the compound (i.e., the adamantane cage is attached to the compound through only one of its vertices), or integral to the compound (i.e., the adamantane cage is bonded in the compound through two or more of its vertices). In one or more embodiments, the adamantyl group in the nonpolymeric compound is an unsubstituted adamantyl. In one or more embodiments, the adamantyl group is also not functionalized. For example, in preferred embodiments, the adamantyl group(s) does not contain acid functionalities, reactive sites, or other moieties, and thus, preferably, does not participate in crosslinking or functionalization of the nonpolymeric compound (discussed in more detail below).

Examples of suitable precursor compounds that include at least two epoxy moieties and at least one adamantyl group include multifunctional epoxy-containing adamantane derivatives, such

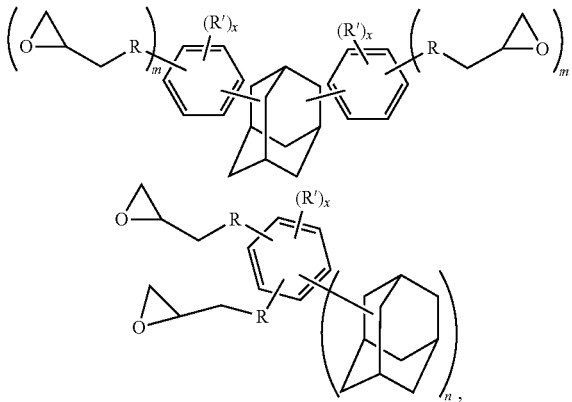

wherein each x is 0-3, each m is at least 2 (preferably 2-4), n is at least 1 (preferably 1-2), each R is individually an oxygen atom or —CH$_2$—. The parenthesis with subscript in the structures above indicate that more than one of the indicated group can be bonded to (radiate from) the compound, and are not used herein to indicated linear/linked/successive repeat units.

Exemplary precursor compounds for use in synthesizing the nonpolymeric compounds include 1,3-bis(1-adamantyl)-4,6-bis(glycidyloxy)benzene, 1,3-bis(2',4'-bis(glycidyloxy)phenyl)adamantane, 1-(2',4'-bis(glycidyloxy)phenyl)adamantane, and 1,3-bis(4'-glycidyloxyphenyl)adamantane. Suitable precursor compounds are commercially available under the tradename Adamantate™ (Idemitsu Kosan Co., Japan). The synthesis of suitable precursor compounds is also described in U.S. Pat. No. 7,790,917, incorporated by reference herein to the extent not inconsistent with the present disclosure.

The nonpolymeric compounds further comprise one or more chemical modification groups bonded to respective epoxide moieties in the compound. The chemical modification groups are reacted with the epoxy to modify/customize the properties of the compound (and resulting composition). For example, light attenuating moieties can be attached to increase the light absorbance of the composition to yield an anti-reflective coating. Likewise, groups can be attached for solubility enhancement, adhesion manipulation (i.e., promotion or reduction), rheology manipulation, crosslinking, and the like.

Suitable chemical modification group precursors will preferably have an acid, phenol, or alcohol groups for reacting with epoxy (e.g., carboxylic acid, amine, thiol, hydroxy, etc.), and in some embodiments, be further substituted with at least one additional reactive moiety that remains unoccupied (unreacted) after bonding to the compound. This reactive moiety can then be used during subsequent crosslinking of the composition, discussed in more detail below. Exemplary reactive moieties include free hydroxyl groups, and the like.

Thus, in some embodiments, the nonpolymeric compounds comprise one or more epoxy moieties bonded with respective light attenuating moieties. In some embodiments, the light attenuating moieties utilized preferably comprise a chromophore having a carboxylic acid, phenol, alcohol, thiol, and/or amine portion for bonding with an epoxy. Preferred chromophores include cyclic compounds (and particularly $C_6$-$C_{18}$ aromatics) and aliphatic (preferably from about $C_1$-$C_{12}$, and more preferably from about $C_1$-$C_8$) acids. For example, acid-functionalized, hydroxy-substituted aromatic compounds are particularly preferred in certain embodiments of the invention. Particularly preferred compounds to act as light attenuating moieties according to the invention include aromatic compounds, such as substituted and unsubstituted: benzoic acid, naphthoic acid, and/or anthracenecarboxylic acid.

In one or more embodiments, the nonpolymeric compounds comprise one or more epoxy moieties bonded with respective solubility enhancing groups, such as hydroxy groups, acids, fatty chains ($C_1$-$C_{12}$), and the like. In one or more embodiments, the nonpolymeric compounds comprise one or more epoxy moieties bonded with respective adhesion promoting groups, such as aliphatic chains, alcohols, polar groups, thiols, and the like. In one or more embodiments, the nonpolymeric compounds comprise one or more epoxy moieties bonded with respective adhesion reducing groups, such as fluorine. In one or more embodiments, the nonpolymeric compounds comprise one or more epoxy moieties bonded with respective rheology manipulating groups, such as aliphatic chains, phenols, hydroxyls, and the like. It will be appreciated that combinations of the foregoing chemical modification groups can be used. For example, more than one type of chemical modification group can be attached to respective epoxy moieties on the same nonpolymeric compound. Likewise, the same epoxy moiety can be bonded to more than one chemical modification group. Alternatively, nonpolymeric compounds comprising one type of chemical modification group can be mixed with nonpolymeric compounds comprising another type of chemical modification group to change properties in the resulting composition.

In one or more embodiments, at least about 10% of the epoxy moieties are occupied (reacted) with a chemical modification group, preferably at least about 50%, and more preferably at least about 75%, based upon the total number of epoxy moieties on all of the nonpolymeric compounds in the composition taken as 100%. In some embodiments, at least about 95% of the epoxy moieties are reacted with a chemical modification group. It will be appreciated that a chemical modification group can be bonded to an epoxy moiety as part of the ring-opening reaction. Alternatively, a chemical modification group can be subsequently bonded to the epoxy moiety via the free hydroxyl group in the ring-opened moiety (i.e., after ring opening). Thus, in some embodiments, two chemical modification groups may be bonded to the nonpolymer compound via the same epoxy moiety.

The nonpolymeric compounds have a weight average molecular weight of from about 500 Daltons to about 2,000 Daltons, preferably from about 600 Daltons to about 1,500 Daltons, and more preferably from about 700 Daltons to about 1,000 Daltons.

In one or more embodiments, the nonpolymeric compounds comprise at least two epoxy moieties, wherein at least one epoxy moiety is of the formula:

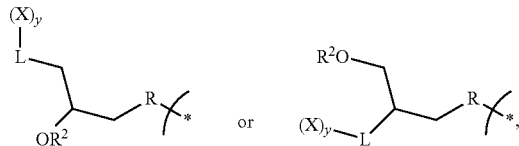

wherein * is the attachment point to the compound, each y is 1-2, each X is a chemical modification group, each L is individually an amino, ether, thio (thioether), hydrazine, sulfinate, sulfonate, sulfonamide, ester, carbonate, carbamate, amide, or urea linkage, each R is individually an oxygen atom or —CH$_2$—, and each R$^2$ is individually an —H, alkyl, sulfonate, ester, carbonate, carbamate, or functionalized derivative thereof. In the case of more than one X group (e.g., when y is 2), each X can be designated as "X$^1$" and "X$^2$" respectively, wherein X$^1$ and X$^2$ can be the same or different, and wherein possible substituents for X$^1$ and X$^2$ are the same as those provided for "X" herein. For example, embodiments of -L-X include: —NX$^1$X$^2$, —OX, —SX, —N—N(X$^1$X$^2$), —S(O)X, or —S(O)$_2$X, —OS(O)$_2$X, —O(C=O)X, —O(C=O)OX, —N(C=O)OX, —N(C=O)X, —N(C=O)N(X$^1$X$^2$), —NX$^1$S(O)$_2$X$^2$, and the like.

In one or more embodiments, each X is independently, hydrogen, Ar (aryl group), (C$_1$-C$_{12}$)-straight or branched alkyl, (C$_1$-C$_{12}$) straight or branched alkenyl or alkynyl, (C$_1$-C$_{12}$) cycloalkyl substituted (C$_1$-C$_{12}$)-straight or branched alkyl, (C$_1$-C$_{12}$) cycloalkyl substituted-(C$_2$-C$_6$) straight or branched alkenyl or alkynyl, (C$_5$-C$_7$)cycloalkenyl substituted-(C$_1$-C$_{12}$) straight or branched alkyl, (C$_5$-C$_7$)cycloalkenyl substituted-(C$_1$-C$_{12}$) straight or branched alkenyl or alkynyl, Ar-substituted (C$_1$-C$_{12}$) straight or branched alkyl, or Ar-substituted-(C$_1$-C$_{12}$) straight or branched alkenyl or alkynyl; wherein any one (or more) of the CH$_2$ groups of the alkynyl, alkenyl or alkyl chains in X is optionally replaced by O, CF$_2$, S, S(O), S(O)$_2$ or N(R$^5$). R$^5$ is optionally substituted by H, S(O)$_2$X, (C=O)X, (C=O)OX, (C=O)N(X)$_2$, Ar, (C$_1$-C$_{12}$)-straight or branched alkyl, (C$_1$-C$_{12}$) straight or branched alkenyl or alkynyl, (C$_1$-C$_{12}$) cycloalkyl substituted (C$_1$-C$_{12}$)-straight or branched alkyl, (C$_1$-C$_{12}$) cycloalkyl substituted-(C$_2$-C$_6$) straight or branched alkenyl or alkynyl, (C$_5$-C$_7$)cycloalkenyl substituted-(C$_1$-C$_{12}$) straight or branched alkyl, (C$_5$-C$_7$)cycloalkenyl substituted-(C$_1$-C$_{12}$) straight or branched alkenyl or alkynyl, Ar-substituted (C$_1$-C$_{12}$) straight or branched alkyl, or Ar-substituted-(C$_1$-C$_{12}$) straight or branched alkenyl or alkynyl; wherein any one (or more) of the CH$_2$ groups of the alkynyl, alkenyl or alkyl chains in X is optionally replaced by O, CF$_2$, S, S(O), S(O)$_2$ or N(R$^5$). In some embodiments, where y is 2, the two X groups can be linked together to form a ring with the L group, such as in the case of a piperidine ring.

Non-limiting examples of X include groups such as phenyl, 1-naphthyl, 2-naphthyl, indenyl, azulenyl, fluorenyl, anthracenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, 2-pyrazolinyl, pyrazolidinyl, isoxazolyl, isothiazolyl, 1,2,3-oxadiazolyl, 1,2,3-triazolyl, 1,2,3-thiadiazolyl, 1,3,4-thiadiazolyl, 1,2,4-triazolyl, 1,2,4-oxadiazolyl, 1,2,4-thiadiazolyl, benzoxazolyl, pyridazinyl, pyrimidinyl, pyrazinyl, 1,3,5-triazinyl, 1,3,5-trithianyl, indolizinyl, indolyl, isoindolyl, 3Hindolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydro-isoquinolinyl, isoquinolinyl, 1,2,3,4-tetrahydro-isoquinolinyl, cinnolinyl, phthalazinyl, quinazolinyl, quinoxalinyl, 1,8-naphthyridinyl, peridinyl, carbazolyl, acridinyl, phenazinyl, phenothiazinyl or phenoxazinyl. It will be appreciated that X could be any chemically feasible mono-, bi- or tricyclic ring system, wherein each ring consists of 5 to 7 ring atoms and wherein each ring comprises 0 to 3 heteroatoms independently selected from N,N(R$^5$), O, S, S(O), or S(O)$_2$. Aryl or cyclic X groups can also be optionally substituted with one to three substituents independently selected from halogen, hydroxyl, nitro, —SO$_3$H, trifluoromethyl, trifluoromethoxy, (C$_1$-C$_6$)-straight or branched alkyl, (C$_1$-C$_6$)-straight or branched alkenyl, O—[(C$_1$-C$_6$)-straight or branched alkyl], O—[(C$_1$-C$_6$)-straight or branched alkenyl], O-benzyl, O-phenyl, 1,2-methylenedioxy, —N(R$^5$—R$^5$), carboxyl, N—(C$_1$-C$_5$)-straight or branched alkyl or (C$_1$-C$_6$)-straight or branched alkenyl) carboxamides, N,N-di-((C$_1$-C$_6$)-straight or branched alkyl or (C$_7$-C$_5$)-straight or branched alkenyl) carboxamides, N—(C$_2$-C$_5$)-straight or branched alkyl or (C$_2$-C$_5$)-straight or branched alkenyl) sulfonamides, N,N-di-(C$_2$-C$_5$)-straight or branched alkyl or (C$_2$-C$_5$)-straight or branched alkenyl) sulfonamides, morpholinyl, piperidinyl, OR$^5$, CH$_2$—(CH$_2$)$_{10}$—R$^5$, O—(CH$_2$)$_{10}$—R$^5$, (CH$_2$)$_{10}$—O—R$^5$, or CH=CH—R$^5$, where R$^5$ is defined above, and wherein any one (or more) of the CH$_2$ groups of the alkynyl, alkenyl or alkyl chains in X is optionally replaced by O, CF$_2$, S, S(O), S(O)$_2$ or N(R$^5$).

For example, in some embodiments where the compositions are used as anti-reflective coatings, X is a chromophore selected from the group consisting of benzene (phenyl group), naphthalene (e.g., 1-naphthyl, 2-naphthyl), anthracene (anthracenyl), alkyls (preferably from about C$_1$-C$_{12}$, and more preferably from about C$_1$-C$_8$), and substituted derivatives thereof.

As noted above, the alcohol group typically present after epoxy ring-opening can be further functionalized if desired, using the alkyl, sulfonate, ester, carbonate, or carbamate groups. For example, functionalized derivatives of such R$^2$ substituents include S(O)$_2$X, (C=O)X, (C=O)OX, (C=O)N(X$^1$X$^2$), Ar, (C$_1$-C$_{12}$)-straight or branched alkyl, (C$_1$-C$_{12}$)

straight or branched alkenyl or alkynyl, ($C_1$-$C_{12}$) cycloalkyl substituted ($C_1$-$C_{12}$)-straight or branched alkyl, ($C_1$-$C_{12}$) cycloalkyl substituted-($C_2$-$C_6$) straight or branched alkenyl or alkynyl, ($C_5$-$C_7$)cycloalkenyl substituted-($C_1$-$C_{10}$) straight or branched alkyl, ($C_5$-$C_7$)cycloalkenyl substituted-($C_1$-$C_{12}$) straight or branched alkenyl or alkynyl, Ar-substituted-($C_1$-$C_{12}$) straight or branched alkyl, or Ar-substituted-($C_1$-$C_{12}$) straight or branched alkenyl or alkynyl; wherein X is defined above and wherein any one of the $CH_2$ groups of the alkynyl, alkenyl or alkyl chains in $R^2$ is optionally replaced by O, $CF_2$, S, S(O), S(O)$_2$ or N($R^5$), where $R^5$ is defined above. Thus, as noted above, the nonpolymeric compounds can be further functionalized with additional X groups in addition to the X groups attached via linkage -L-.

In one or more embodiments, the nonpolymeric compound further comprises a core component to which the epoxy and adamantyl moieties are respectively bonded. In other words, the epoxy moieties are preferably not directly connected to the adamantyl cage rings. The structure of the core component is not important, so long as it is capable of bonding with the epoxy and adamantyl moieties. Exemplary core components include structures selected from the group consisting of aromatic or aliphatic cyclic compounds, acyclic compounds, and functional derivatives of the foregoing. Specific examples of suitable core components include functional derivatives of cycloalkanes, heterocycles, aromatic rings (e.g., benzene), branched or linear alkyls, alkenes, alkynes, and the like. The term "functional derivatives" refers to a derivative of the compound whose structure has been altered so that it may bond with another compound. For example, a functional derivative of benzene would include a benzene ring where one or more hydrogen atoms have been removed so that a carbon atom of the benzene ring can bond with another compound or moiety. In some embodiments, the nonpolymeric compound consists essentially of, or even consists of, the core component, at least two epoxy moieties, at least one adamantyl group, and at least one chemical modification group bonded to one of the epoxies.

In one or more embodiments, nonpolymeric compounds according to the invention will comprise (consist essentially, or even consist of) the following general formula:

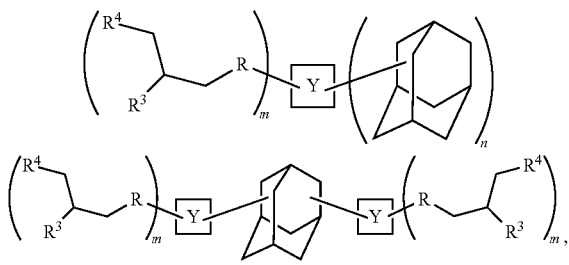

where m is at least 2 (preferably 2-4), n is at least 1 (preferably 1-2), [Y] is the core component as defined above; each R is individually an oxygen atom or —$CH_2$—, $R^3$ and $R^4$ are different from each other in a given compound and each selected from the group consisting of -L-(X)$_y$ and —$OR^2$, where each L is individually an amino, ether, thio (thioether), hydrazine, sulfinate, sulfonate, sulfonamide, ester, carbonate, carbamate, amide, or urea linkage, y is 1-2, X is a chemical modification group, and each $R^2$ is individually an —H, alkyl, sulfonate, ester, carbonate, carbamate, or functionalized derivative thereof.

Regardless of the embodiment, these compounds can be utilized to make compositions for use in microlithographic processes, such as anti-reflective coatings or planarization layers. The compositions are formed by simply dispersing or dissolving the nonpolymeric compound(s) in a suitable solvent system, preferably at ambient conditions and for a sufficient amount of time to form a substantially homogeneous dispersion. Preferred compositions comprise from about 0.5 to about 50% by weight of the nonpolymeric compound, preferably from about 1 to about 20% by weight of the nonpolymeric compound, and more preferably from about 1 to about 5% by weight of the nonpolymeric compound, based upon the total weight of solids in the composition taken as 100% by weight. In one or more embodiments, compositions according to the invention are preferably substantially nonpolymeric (i.e., comprise less than about 10% by weight polymeric ingredients, more preferably less than about 5%, and even more preferably less than about 1% by weight polymeric ingredients, based upon the total weight of the solids in the composition taken as 100% by weight).

The solvent system can include any solvent suitable for use in microelectronics manufacturing. Preferably, the solvent system has a boiling point of from about 100° C. to about 200° C. In one or more embodiments, the solvent system will comprise a solvent selected from the group consisting of propylene glycol monomethyl ether (PGME), propylene glycol monomethyl ether acetate (PGMEA), ethyl lactate, propylene glycol n-propyl ether (PnP), cyclohexanone, tetrahydrofuran (THF), dimethyl formamide (DMF), γ-butyrolactone, and mixtures thereof.

Any additional ingredients can be dispersed in the solvent system along with the nonpolymeric compound. Examples of suitable additional ingredients include crosslinking agents, catalysts, polymeric additives, and surfactants. In some embodiments, the composition is substantially free of polymeric additives. In other words, such ingredients are present at levels of less than about 0.01% by weight, and preferably less than about 0.001% by weight, based upon the total solids taken as 100% by weight. In one or more embodiments, the anti-reflective or planarization compositions consist essentially of, or even consist of, the nonpolymeric compound dispersed or dissolved in a solvent system along with only those additional ingredients described herein for inclusion in the composition. In other words, in some embodiments, the present composition excludes any other ingredients not specifically enumerated herein.

For example, in some embodiments, the composition consists essentially of, or even consists of, the nonpolymeric compound dispersed or dissolved in a solvent system along with a crosslinking agent. When present, the composition will comprise less than about 40% by weight crosslinking agent, preferably from about 0.05 to about 40% by weight crosslinking agent, and more preferably from about 5 to about 30% by weight, based upon the total weight of solids in the composition taken as 100% by weight. Exemplary crosslinking agents that can be used in some embodiments of the invention include aminoplasts (e.g., POWDERLINK® 1174, Cymel® products), multifunctional epoxy resins (e.g., MY720, CY179MA, DENACOL), anhydrides, vinyl ethers (e.g., multifunctional vinyl ethers, such as VECTomer™), and mixtures thereof.

Examples of preferred catalysts include sulfonic acids (e.g., p-toluenesulfonic acid, styrene sulfonic acid), photoacid generators (e.g., triphenyl sulfonium triflate, triphenyl sulfonium nonaflate), thermal acid generators (e.g., pyridinium tosylate), carboxylic acids (e.g., trichloroacetic acid, benzene tetracarboxylic acid), phosphoric acids, and mixtures thereof. When present, the composition will comprise less than about 10% by weight catalyst, preferably from about 0.01 to about 10% by weight catalyst, and more preferably from about 0.01 to about 5% by weight, based upon the total weight of solids in the composition taken as 100% by weight.

In one or more embodiments, surfactants can be included in the composition to improve the coat quality of the composition. Exemplary surfactants that can be used include perfluoro alkyls and the like. When present, the composition will comprise less than about 1% by weight surfactant, preferably from about 0.001 to about 1% by weight surfactant, and more preferably from about 0.001 to about 0.05% by weight surfactant, based upon the total weight of the composition taken as 100% by weight.

As previously mentioned, the compositions are particularly useful as anti-reflective or planarization coatings in microelectronic fabrication. For example, a coating can be formed on a substrate by applying a quantity of the inventive composition to the substrate to form a layer of the composition on the substrate surface. The composition may be applied directly to the substrate surface, or to uppermost layer of one or more optional intermediate underlayers that have been formed on the substrate surface. Suitable intermediate underlayers include those selected from the group consisting of spin-on carbon layers (SOC), amorphous carbon layers, planarization layers, bottom anti-reflective coatings, and combinations of the foregoing. In some embodiments, however, the anti-reflective or planarization composition can be present in the microelectronic structure in lieu of any carbon-rich layers. In other words, the microelectronic structure can be free of other carbon-rich layers in the stack. The term "carbon-rich," as used herein, refers to compositions comprising greater than about 50% by weight carbon, preferably greater than about 70% by weight carbon, and more preferably from about 75 to about 80% by weight carbon, based upon the total solids in the composition taken as 100% by weight.

Any microelectronic substrate can be used in the invention. Preferred substrates include those selected from the group consisting of silicon, SiGe, $SiO_2$, $Si_3N_4$, aluminum, tungsten, tungsten silicide, gallium arsenide, germanium, tantalum, tantalum nitride, coral, black diamond, phosphorous or boron doped glass, ion implant layers, titanium nitride, hafnium oxide, silicon oxynitride, and mixtures of the foregoing. The composition can be applied by any known application method, with one preferred method being spin-coating the composition at speeds of from about 750 rpm to about 5,000 rpm (preferably from about 750 rpm to about 4,000 rpm, and more preferably from about 1,000 rpm to about 3,500 rpm) for a time period of from about 20 seconds to about 90 seconds (preferably from about 30 seconds to about 60 seconds). The substrate can have a planar surface, or it can include topography features (via holes, trenches, contact holes, raised features, lines, etc.). As used herein, "topography" refers to the height or depth of a structure in or on a substrate surface. For example, the substrate can comprise structure defining a hole, which includes sidewalls and a bottom wall. Thus, the method of applying the anti-reflective or planarization composition to the substrate would preferably include applying the composition to at least a portion of those hole sidewalls and bottom wall.

After the desired coverage is achieved, the layer of composition is then heated to evaporate solvents and form a cured layer. The layer is preferably heated to temperatures of at least about 125° C., preferably from about 150° C. to about 230° C., and more preferably from about 150° C. to about 205° C., and for a time period of from about 30 seconds to about 90 seconds (preferably from about 45 seconds to about 75 seconds). In one or more embodiments, curing of the inventive layer involves crosslinking of the nonpolymeric compounds in the composition. Thus, in some embodiments, the layer is heated to at least about the crosslinking temperature of the composition (e.g., at least about 150° C.). It will be appreciated that crosslinking of the nonpolymeric compounds can occur through the free reactive moieties (e.g., —OH groups) on the chemical modification groups in the compound. Likewise, crosslinking can be initiated through the free —OH groups on the ring-opened epoxy moieties, or through other suitable functional groups on the chemical modification moiety. Thus, suitable crosslinking sites will vary depending upon the type of crosslinker chosen (if necessary). In some embodiments, the nonpolymeric compounds can self-crosslink without the aid of a crosslinker, depending upon the chemical modification group's reactive moieties. As mentioned above, the adamantyl groups preferably do not participate in crosslinking.

Regardless of the embodiment, the average thickness of the cured inventive coating or film is preferably from about 5 nm to about 5 μm, more preferably from about 10 nm to about 3 μm, and even more preferably from about 20 nm to about 2 μm. If the substrate includes topography, the inventive coating preferably has a thickness sufficient to substantially cover the substrate topography at these thicknesses. The average thickness is defined as the average of 5 measurements across the substrate taken by an ellipsometer.

Cured layers according to the invention will be substantially insoluble in solvents (e.g., ethyl lactate, PGME) typically utilized in photoresists. Thus, when subjected to a stripping test, the inventive coating will have a percent stripping of less than about 5%, preferably less than about 1%, and even more preferably about 0%. The stripping test involves first determining the thickness (by taking the average of measurements at five different locations) of a cured layer. This is the average initial film thickness. Next, a solvent (e.g., PGME) is puddled onto the cured film for about 20 seconds, followed by spin drying at about 3,000 rpm for about 30 seconds to remove the solvent. The thickness is measured again at five different points on the wafer using ellipsometry, and the average of these measurements is determined. This is the average final film thickness. The amount of stripping is the difference between the initial and final average film thicknesses. The percent stripping is:

$$\% \text{ stripping} = \left(\frac{\text{amount of stripping}}{\text{initial average film thickness}}\right) \times 100.$$

The cured inventive layer is also preferably substantially insoluble in typical photoresist developers (e.g., tetramethylammonium hydroxide (TMAH)). The solubility of the inventive film in developer is evaluated using the same procedure and calculation as that for the stripping test described above, except that instead of a photoresist solvent, a developer is used. The crosslinked layer is also subjected to a PEB at 110° C. for 60 seconds. Next, 0.26 N TMAH developer is puddled onto the layer for 45 seconds, followed by a 5-second deionized water rinse, and a spin dry. Any loss of thickness in the cured layer is defined as the "dark loss." The cured layer will have a dark loss of less than about 5%, preferably less than about 1.5%, more preferably less than about 1%, even more preferably less than about 0.8%, and most preferably about 0%.

Coatings according to the invention have high etch rates. Thus, the cured coatings have an etch rate of at least about 2

Å/second, preferably from about 2 to about 10 Å/second, more preferably from about 3 Å/second to about 7 Å/second, and even more preferably from about 4 Å/second to about 6 Å/second, when $CF_4$ is used as the etchant. When $O_2$ is used as the etchant, the cured coatings have an etch rate of at least about 10 Å/second, preferably from about 10 to about 50 Å/second, more preferably from about 15 Å/second to about 40 Å/second, and even more preferably from about 20 Å/second to about 35 Å/second. When use as anti-reflective coatings, the layers preferably possess light absorbing properties. For example, the refractive index (n value) of a cured anti-reflective layer at 193 nm or 248 nm will be at least about 1.2, preferably from about 1.3 to about 2, and more preferably from about 1.4 to about 1.8. The anti-reflective layers have an extinction coefficient (k value) of at least about 0.001, preferably from about 0.01 to about 0.8, and more preferably from about 0.05 to about 0.6, at the wavelength of use (e.g., 193 nm, 248 nm, or 365 nm). The coatings can be used to obtain a resolution of less than about 100 μm and preferably less than about 50 μm in a 193 nm photoresist.

A photosensitive composition can then be applied to the inventive layer, followed by a post-application baked (PAB), to form an imaging layer. The thickness of the imaging layer will typically range from about 50 nm to about 2,000 nm. Suitable imaging compositions include commercially-available photoresists (e.g., TarF-Pi6-001 from TOK, Kawasaki shi, Kanagawa (Japan); ARX3001JN, ARX3340J, and AM2073J, from JSR Micro, Sunnyvale, Calif.; SAIL-X-181, Shin-Etsu, Tokyo (Japan)), or any other photosensitive compositions. The imaging layer can be patterned by exposure to light of the appropriate wavelength, followed by a post-exposure bake (PEB), and development of the pattern. Suitable developers are organic or inorganic alkaline solutions such as potassium hydroxide (KOH), TMAH, and preferably comprise an aqueous solution of TMAH at a concentration of 0.26N or lower. Some of these developers are commercialized under the tradenames PD523AD (available from Moses Lake Industries, Inc., Moses Lake, Wash.), MF-319 (available from Dow Chemical), MF-320 (available from Shipley), and NMD3 (available from TOK, Japan).

In another embodiment, ArF immersion lithography (not shown) can be used to pattern the imaging layer. Instead of air (as in conventional lithography), the medium through which the radiation passes during exposure is a liquid. The imaging layer is exposed to radiation via an optical projection element (i.e., lens) of a lithographic system, with the immersion liquid contacting at least a portion of the optical element of the lithographic system and a portion of the structure (i.e., the stack). Even more preferably, the liquid fills the space between the last optical element in the system and the imaging layer, such that the optical element is immersed in the liquid. Suitable immersion liquids preferably have a refractive index greater of than 1 (preferably from about 1 to about 2, and more preferably from about 1.3 to about 1.4), and are selected from the group consisting of water (preferably purified water) or organic solvents. Immersion lithography systems are known in the art and include the Amphibian Interferometer from Amphibian™ Systems (Rochester, N.Y.), and the 1900i from ASML (Veldhoven, Netherlands).

In one or more embodiments, the imaging layer is formed directly on the inventive layer. In alternative embodiments, one or more intermediate layers are first formed on the inventive layer before forming the imaging layer. For example, optional intermediate layers that can be included in the stack between the photoresist and the inventive layer include hardmasks, anti-reflective coatings (e.g., when the inventive layer is a planarization layer), spin-on carbon, and the like. In one or more embodiments, the inventive layer has a sufficient etch rate that a separate hardmask is not necessary in the stack. Thus, in some embodiments, the microelectronic structure does not contain (i.e., is free of) any other hardmask layers.

Regardless, once the imaging layer is patterned, the pattern can be transferred to subsequent layers in the stack to transfer the pattern into the substrate and complete the device manufacture. If present, photosensitive, developer-soluble layers in the stack can be removed substantially simultaneously with the photoresist during development. Other layers in the stack, such as hardmasks, as well as the inventive coating can then be selectively removed during dry etching using the imaging layer or other patterned layer as a mask. Thus, in one or more embodiments, the inventive coatings are not photosensitive (i.e., are not decrosslinked or patterned by light exposure). The etch ratio of the imaging layer (e.g., 193 nm photoresist) to the inventive layer will be from about 1:2 to about 4:1, preferably from about 1:1 to about 3:1, when $CF_4$ plasma is used as the etchant. The exposure-development process can also be repeated using a second imaging layer applied adjacent to the patterned inventive coating (or optional intermediate layer) if a multiple exposure process is desired. The pattern can then be transferred into the substrate.

Additional advantages of the various embodiments of the disclosure will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment, including embodiments of certain claim groupings, may also be included in other embodiments (or claim groupings), but is not necessarily included. Thus, the present invention encompasses a variety of combinations and/or integrations of the specific embodiments described herein. In addition, while the drawings illustrate, and the specification describes, certain preferred embodiments, it is to be understood that such disclosure is by way of example only.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Synthesis of Mother Liquor 1

In this Example, 20.06 grams of Adamantate E-201 (Idemitsu Kosan Co., Japan), 16.12 grams of 3,7-dihydroxy-2-naphthoic acid (Sigma Aldrich, St, Louis, Mo.), 0.44 grams of benzyltrimethylammonium chloride (Sigma Aldrich, St. Louis, Mo.), and 54.26 grams of propylene glycol monomethyl ether (PGME) (Ultrapure Solutions, Houston, Tex.) were added to a 250-ml round bottom flask. The flask was fitted with a condenser, purged with nitrogen, and immersed into an oil bath heated to 120° C. The mixture was stirred and allowed to react for 16 hours. The resulting product was a low viscosity yellow/brown liquid. This final product was ion exchanged to remove the catalyst and residual 3,7-dihydroxy-2-naphthoic acid by immersion of a 10% loading of both 200H and 550A ion exchange beads (Dow Chemical) for 4 hours.

Example 2

Carbon Layer Formulation Using Mother Liquor 1

The mother liquor from Example 1 was formulated into a curable solution for spin-coating. The formulation was made by mixing 8.48 grams of mother liquor 1 with 0.681 grams Powderlink 1170 (Cytec Industries, Orange, Calif.), 5.1 grams of a 2% 5-sulfosalicylic acid in PGME solution (King Industries, Norwalk, Conn.), 2.66 grams PGMEA, and 13.25 grams of PGME. The mixture was spin coated onto 4-inch silicon wafers at a spin speed of 1,500 rpm and a ramp rate of 5,000 rpm/s for 60 seconds, followed by a bake at 205° C. for 60 seconds. The resulting film thickness (5,737 Å) was measured using a J. A. Woolam M2000 VASE. The film was also tested to determine the extent of curing by puddling PGME on the wafer for 20 seconds, spinning dry, and re-measuring the thickness. The change (decrease) in thickness was only 34 Å, which indicated a complete cure.

Example 3

Synthesis of Mother Liquor 2

In this procedure, 30.01 grams of Adamantate E-201, 25.82 grams of 9-anthracenecarboxylic acid (St. Jean Photochimical, Saint-Jean-sur-Richelieu, Quebec, Canada), 1.17 grams of benzyltrimethylammonium chloride, and 85.03 grams of PGME were added to a 250-ml round bottom flask. The flask was fitted with a condenser, purged with nitrogen, and immersed into an oil bath heated to 120° C. The mixture was stirred and allowed to react for 16 hours. The reaction scheme is shown in FIG. 1. The resulting product was a low viscosity yellow liquid. This final product was ion exchanged to remove the catalyst and residual 9-anthracenecarboxylic acid by immersion of a 10% loading of both 200H and 550A ion exchange beads (Dow Chemical) for 4 hours.

Example 4

Formulation Using Mother Liquor 2

The mother liquor from Example 3 was formulated into a curable solution for spin-coating. The formulation was made by mixing 8.47 grams of mother liquor 2 with 0.684 grams of Powderlink 1170 (Cytec), 5.07 grams of a 2% 5-sulfosalicylic acid in PGME solution, 2.59 grams of PGMEA, and 13.36 grams of PGME. The mixture was spin coated onto 4-inch silicon wafers at a spin speed of 1.500 rpm and a ramp rate of 5,000 rpm/s for 60 seconds, followed by a bake at 205° C. for 60 seconds. The resulting film thickness (5,208 Å) was measured using a M2000 VASE. The extent of curing was tested by puddling PGME onto the wafer for 20 seconds, spinning dry, and remeasuring the thickness. The change (decrease) in thickness was only 7 Å, indicating a complete cure.

Example 5

Synthesis of Mother Liquor 3

Figure 2:
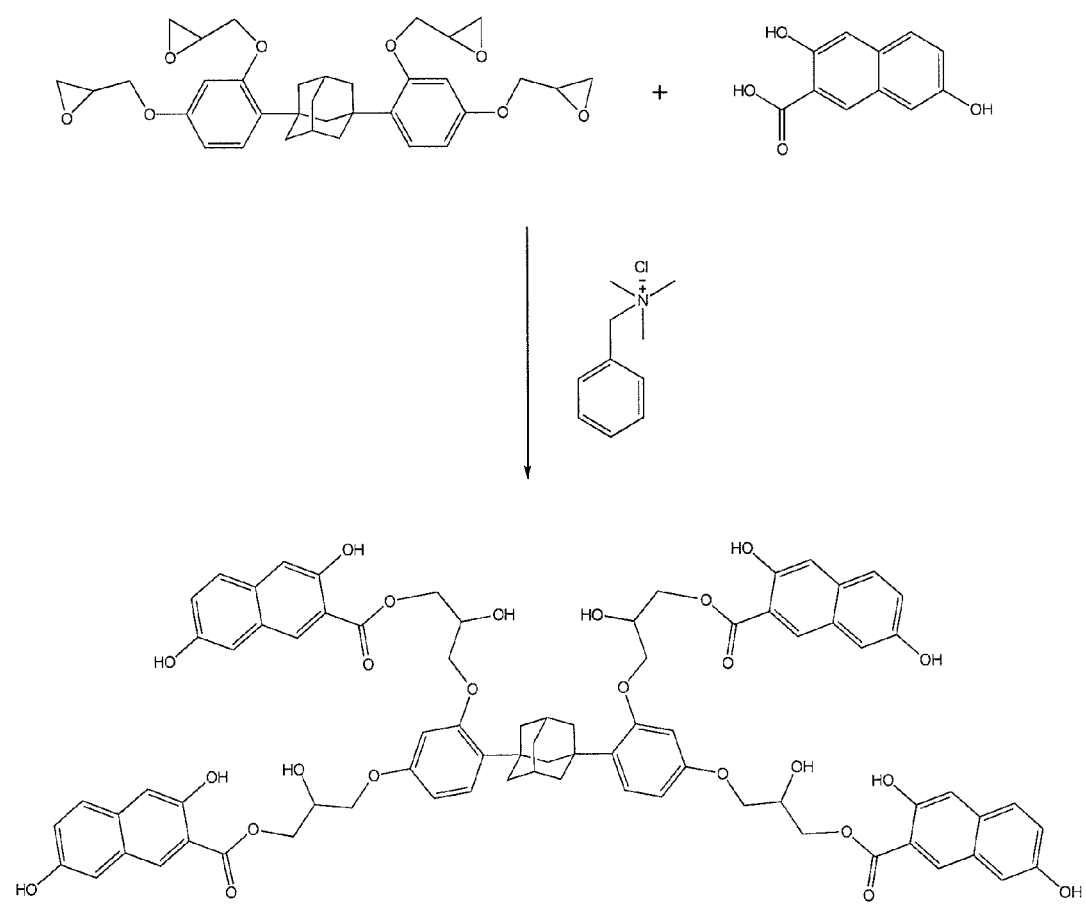
FIG. 2 is a reaction scheme for formation of a nonpolymeric compound according to an embodiment of the invention by reacting 3,7-dihydroxy-2-naphthoic acid with 1,3-bis(2',4'-bis(glycidyloxy)phenyl)adamantane.

In this procedure, 24.5 grams of Adamantate E-401 (Idemitsu Kosan Co., Japan), 33.0 grams of 3,7-dihydroxy-2-naphthoic acid, 0.96 gram of benzyltrimethylammonium chloride, and 134.0 grams of cyclohexanone (Honeywell, Morristown, N.J.) were added to a 250-ml round bottom flask. The flask was fitted with a condenser, purged with nitrogen, and immersed into an oil bath heated to 120° C. The mixture was stirred and allowed to react for 16 hours. The reaction scheme is illustrated in FIG. 2. The resulting product was a low viscosity yellow/brown liquid. This final product was ion exchanged to remove the catalyst by immersion of a 15% loading of 200H ion exchange beads (Dow Chemical) overnight.

Example 6

Formulation Using Mother Liquor 3

The mother liquor from Example 5 was formulated into a curable solution for spin-coating. The formulation was made by mixing 0.34 grams of mother liquor 3 with 4.0 grains of a 1% trivinyl ether crosslinker (Brewer Science, Inc.) solution in PGME, 2.0 grams of a 0.1% triphenylsulfonium nonaflate solution in PGME, and 3.66 grams of PGME. The mixture was spin coated onto 4-inch silicon wafers at a spin speed of 1,500 rpm and a ramp rate of 5,000 rpm/s for 60 seconds, followed by a bake at 205° C. for 60 seconds. The resulting film thickness (441 Å) was measured using a M2000 VASE. The film was also tested for the extent of curing by puddling ethyl lactate on the wafer for 20 seconds, spinning dry, and remeasuring the thickness. The change (decrease) in thickness was only 8 Å, indicating a complete cure.

Example 7

Lithography Results

The formulation from Example 4 was spin coated onto two silicon wafers at a spin speed of 1,750 rpm for 30 seconds and then the wafers were baked at 205° C. for 60 seconds to create a target thickness of approximately 110 nm. One wafer was then coated with an experimental hardmask material designated as OptiStack® 900-series (available from Brewer Science Inc., Rolla, Mo.) by spin coating it at 1,500 rpm for 30 seconds and then baking it on a hot plate at 205° C. for 60 seconds to create a target hardmask thickness of 40 nm. The second wafer was then coated with OptiStack® HM9825-302.6 material (Brewer Science) by spin coating it at 1,500 rpm for 30 seconds and then baking it on a hot plate at 205° C. for 60 seconds to create a target hardmask thickness of 26 nm. Both of these wafers were then coated with TArF Pi6-133 photoresist (TOK, Japan) by spin coating at 1,500 rpm for 26 seconds and then baking them at 120° C. for 60 seconds to create a resist layer of approximately 100 nm.

Each wafer was then exposed on an ASML XT:1900i Step-and-Scan system and developed using the parameters listed in Table 1.

TABLE 1

| Parameter | Conditions L/S | Notes |
|---|---|---|
| Resist: | TarF Pi6-133 | |
| Resist thickness (nm): | 100 | |
| Resist coat (rpm/s): | 1500/26 | |
| Target (nm/pitch): | 40L/80P | |
| PAB (° C./s): | 120/60 | |
| Illumination mode: | Dipole35Y Gen2 | Job: IMEC790 |
| NA: | 1.35 | |
| Sigma (outer/inner): | 0.97/0.78 | |
| Layer | TM07-40 | |
| Polarization: | x-polarized | |
| Center dose/step (mJ/cm$^2$) | 24/1 | |
| Focus offset/step (μm): | −0.02/0.03 | |
| Reticle bar code: | TM07EAPSMV1L: | |
| PEB (° C./s): | 85/60 | |
| Dev./Rinse Time (s): | OPD5262-35/SS | |

Figure 3:
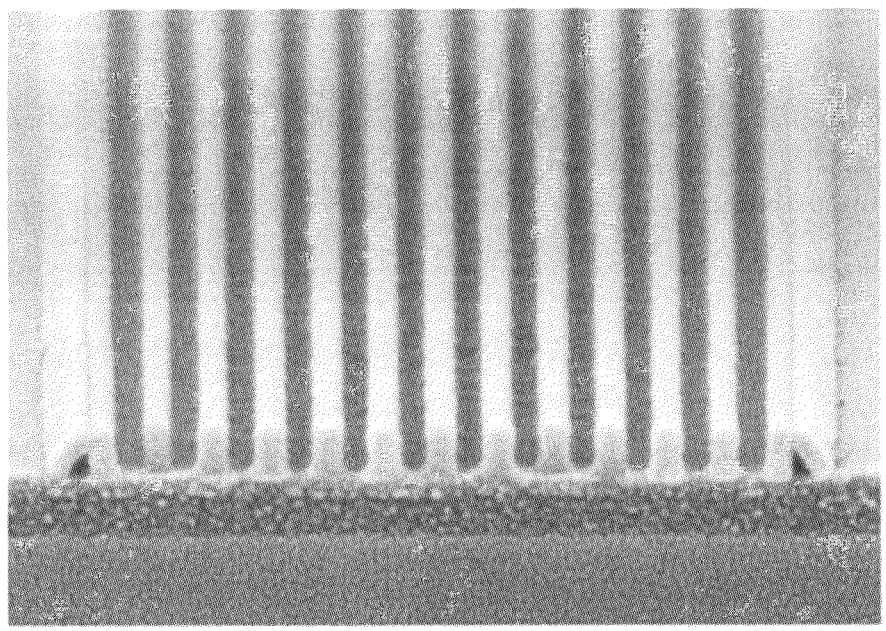
FIG. 3 is a scanning electron microscope (SEM) cross-section image of the inventive nonpolymeric coating composition imaged using an experimental hardmask.
Figure 4:
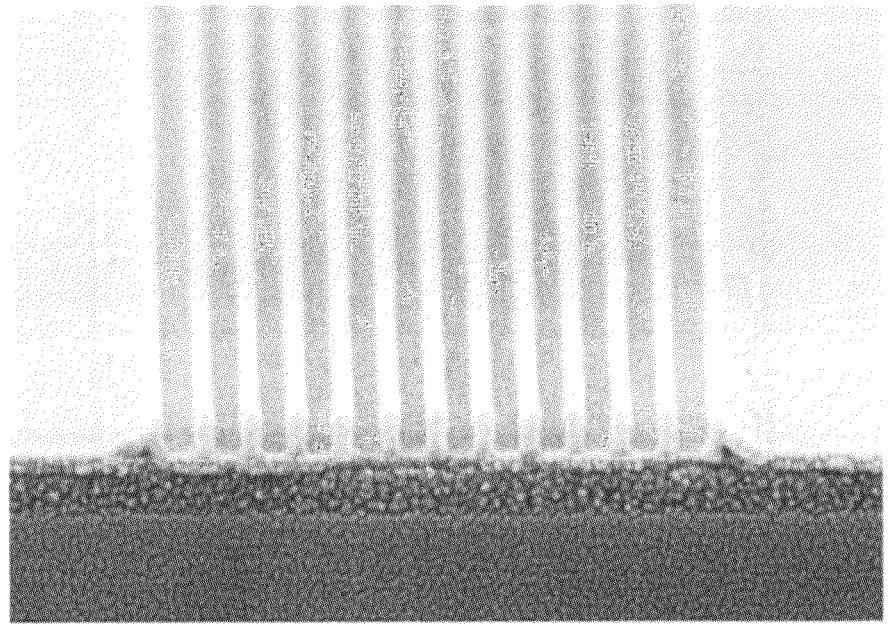
FIG. 4 is an SEM cross-section image of the inventive nonpolymeric coating composition imaged using a commercially-available hardmask.

FIG. 3 shows 40-nm features created using the experimental hardmask with the inventive carbon formulation layer. FIG. 4 shows 40-nm features created using the OptiStack® HM9825 hardmask layer with the inventive carbon formulation layer.

Example 8

Etch Resistance

The etch resistance of the formulation from Example 4 (at varying dilutions) was tested and compared to a commercially-available spin-on carbon composition (Optistack® 110D). Each composition was applied to a silicon wafer and cured, followed by measuring the initial average thickness of each film with an ellipsometer. Each coated wafer was then etched using an Oxford Plasmalab® 80 Plus reactive ion etching (RIE) system with $O_2$ gas at a 50 sccm flow rate, at 100 watts of power and 50 mTorr of pressure. After etching, the final film thickness was measured. The etch rate was the difference between initial thickness and the final thickness divided by the etch time. The results are given in Table 2.

TABLE 2

| Name | Time (s) | Initial Avg Thickness | DC-Bias | Final Avg Thickness | Difference | Å/sec | nm/min | Average |
|---|---|---|---|---|---|---|---|---|
| 110D | 30 | 2172 | 366 | 1283 | 889 | 29.63 | 177.8 | |
| 110D | 30 | 2179 | 366 | 1308 | 871 | 29.04 | 174.2 | |
| 110D | 30 | 2170 | 367 | 1306 | 864 | 28.80 | 172.8 | 174.9 |
| Example 4 | 60 | 5997 | 368 | 4438 | 1558 | 25.97 | 155.8 | |
| Example 4 | 60 | 6003 | 369 | 4445 | 1557 | 25.95 | 155.7 | |
| Example 4 | 60 | 5974 | 368 | 4422 | 1552 | 25.86 | 155.2 | 155.6 |
| Example 4 | 120 | 23843 | 369 | 20888 | 2955 | 24.63 | 147.8 | |
| Example 4 | 120 | 24074 | 370 | 20995 | 3079 | 25.66 | 153.9 | |
| Example 4 | 120 | 24005 | 368 | 20809 | 3196 | 26.64 | 159.8 | 153.8 |

What is claimed:

1. A planarizing and/or anti-reflective composition useful in forming microelectronic structures, said planarizing and/or anti-reflective composition comprising a nonpolymeric compound, a catalyst, and a crosslinking agent dispersed or dissolved in a solvent system, said nonpolymeric compound comprising at least two epoxy moieties and at least one adamantyl group, wherein at least one of said epoxy moieties is of the formula:

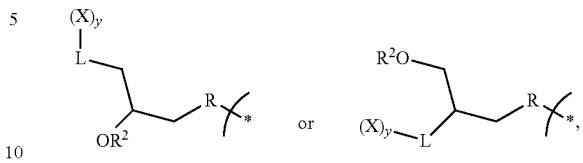

wherein:
* is the attachment point to the compound;
each y is 1-2;
each R is individually —O— or —$CH_2$—;
each $R^2$ is individually an —H, alkyl, sulfonate, ester, carbonate, carbamate, or functionalized derivative thereof;
each L is individually an amino, ether, thio, hydrazine, sulfinate, sulfonate, sulfonamide, ester, carbonate, carbamate, amide, or urea linkage;
each X is a chemical modification group selected from the group consisting of light attenuating moieties, solubility enhancing moieties, adhesion promoting moieties, rheology modifiers, and combinations thereof, said light attenuating moieties being selected from the group consisting of benzene, naphthalene, anthracene, $C_1$-$C_{12}$ alkyls, and substituted derivatives thereof, said solubility enhancing moieties being selected from the group consisting of hydroxy groups, acids, and fatty chains, said adhesion promoting moieties being selected from the group consisting of alcohols, polar groups, and thiols, and said rheology modifiers being selected from the group consisting of phenols and hydroxyls;
said catalyst is selected from the group consisting of sulfonic acids, photoacid generators, thermal acid generators, carboxylic acids, phosphoric acids, and mixtures thereof; and
said crosslinking agent is selected from the group consisting of aminoplasts, multifunctional epoxy resins, anhydrides, vinyl ethers, and mixtures thereof.

2. A method of forming a microelectronic structure, said method comprising:
providing a microelectronic substrate having a surface;
optionally forming one or more intermediate underlayers on said substrate surface; and
forming an anti-reflective or planarization layer adjacent said intermediate underlayers, if present, or adjacent said substrate surface if no intermediate underlayers are present, said anti-reflective or planarization layer being formed from the composition according to claim 1.

3. The method of claim 2, further comprising:
optionally forming one or more intermediate layers adjacent said anti-reflective or planarization layer;

applying an imaging layer adjacent said intermediate layers, or adjacent said anti-reflective or planarization layer if no intermediate layers are present; and patterning said imaging layer to yield a pattern in said imaging layer.

4. The method of claim 3, wherein said intermediate layers are selected from the group consisting of hardmasks, spin-on carbon, anti-reflective coatings, and combinations thereof.

5. The method of claim 3, wherein said patterning comprises:

selectively exposing said imaging layer to activating radiation;

post-exposure baking said imaging layer; and contacting said imaging layer with a photoresist developer to yield said pattern.

6. The method of claim 3, further comprising transferring said pattern into said intermediate layers, if present, and into said anti-reflective or planarization layer, wherein said transferring comprising dry etching said anti-reflective or planarization layer to yield a patterned anti-reflective or planarization layer.

7. The method of claim 6, wherein the etch ratio of said imaging layer to said anti-reflective or planarization layer is from about 1:2 to about 4:1, when $CF_4$ plasma is used as an etchant.

8. The method of claim 6, further comprising transferring said pattern into said intermediate underlayers, if present, and into said substrate via dry etching using said patterned anti-reflective or planarization layer as an etch mask.

9. The method of claim 2, wherein said anti-reflective or planarization layer is not photosensitive.

10. The composition of claim 1, said nonpolymeric compound further comprising a core component to which said epoxy moieties and said adamantyl group are respectively bonded.

11. The composition of claim 10, wherein said core component is selected from the group consisting of aromatic or aliphatic cyclic compounds, acyclic compounds, and functional derivatives of the foregoing.

12. The composition of claim 10, wherein said core component is a functional derivative of benzene, a cycloalkane, a heterocycle, branched or linear alkyls, alkenes, or alkynes.

13. The composition of claim 1, wherein said solvent system includes a solvent selected from the group consisting of propylene glycol monomethyl ether, propylene glycol monomethyl ether acetate, ethyl lactate, propylene glycol n-propyl ether, cyclohexanone, tetrahydrofuran, dimethyl formamide, γ-butyrolactone, and mixtures thereof.

14. The composition of claim 1, further comprising, surfactants.

15. The composition of claim 1, said composition comprising less than about 10% by weight polymeric ingredients, based upon the total weight of the solids in the composition taken as 100% by weight.

16. The composition of claim 1, wherein each $R^2$ is individually an —H, alkyl, $S(O)_2X$, $(C=O)X$, $(C=O)OX$, $(C=O)N(X^1X^2)$, or functionalized derivative thereof; and $X$, $X^1$, and $X^2$ are independently selected from the group consisting of light attenuating moieties, solubility enhancing moieties, adhesion promoting moieties, rheology modifiers, and combinations thereof, said light attenuating moieties being selected from the group consisting of benzene, naphthalene, anthracene, $C_1$-$C_{12}$ alkyls, and substituted derivatives thereof, said solubility enhancing moieties being selected from the group consisting of hydroxy groups, acids, and fatty chains, said adhesion promoting moieties being selected from the group consisting of alcohols, polar groups, and thiols, and said rheology modifiers being selected from the group consisting of phenols and hydroxyls.

17. The composition of claim 1, wherein said composition being curable to form a layer having a n value of from about 1.3 to about 2 at a wavelength of 193 nm or 248 nm.

18. The composition of claim 1, wherein said composition being curable to form a layer having a k value of from about 0.01 to about 0.8.

* * * * *